(12) United States Patent
Huq et al.

(10) Patent No.: US 6,486,128 B1
(45) Date of Patent: Nov. 26, 2002

(54) METHOD OF USING EMAMECTIN TO TREAT FISH PARASITES

(75) Inventors: Abu S. Huq, Plainsboro, NJ (US); Zezhi J. Shao, Basking Ridge, NJ (US); Kanwal J. Varma, Warren, NJ (US)

(73) Assignee: Schering-Plough Veterinary Corporation, Reno, NV (US)

( * ) Notice: Subject to any disclaimer, the term of this patent is extended or adjusted under 35 U.S.C. 154(b) by 0 days.

(21) Appl. No.: 09/544,035

(22) Filed: Apr. 6, 2000

Related U.S. Application Data

(60) Provisional application No. 60/128,255, filed on Apr. 8, 1999.

(51) Int. Cl.⁷ .............................................. A61K 31/70
(52) U.S. Cl. ..................................................... 514/30
(58) Field of Search ........................................... 514/30

(56) References Cited

U.S. PATENT DOCUMENTS

| | | | |
|---|---|---|---|
| 5,288,710 A | 2/1994 | Cvetovich ..................... | 514/30 |
| 5,399,717 A | 3/1995 | Cvetovich et al. ........... | 549/264 |
| 5,962,499 A | 10/1999 | Meinke et al. ............... | 514/410 |
| 5,977,029 A | 11/1999 | Fischer et al. ............... | 504/292 |

FOREIGN PATENT DOCUMENTS

| | | |
|---|---|---|
| WO | WO 92 08352 A | 5/1992 |

OTHER PUBLICATIONS

I.H. Sutherland, "Veterinary Use of Ivermectin," *Acta Leidensia*, vol. 59, Nos. 1 and 2, pp. 211–216 (1990).
M.W. Jones et al., "Reduced sensitivity of the salmon louse, Lepeophtheirus salmonis, to the organophosphate dichlorvos," *Journal of Fish Diseases*, vol. 15, pp. 197–202 (1992).
M. Roth et al., "Current practices in the chemotherapeutic control of sea lice infestations in aquaculture: a review," *Journal of Fish Diseases*, vol. 16, pp. 1–26 (1993).
J.M. Thomassen, "Hydrogen peroxide as a delousing agent for Atlantic salmon," *Pathogens of Wild and Farmed Salmon: Sea Lice*, pp. 290–295 (1993).
S.C. Johnson et al., "Toxicity and pathological effects of orally administered ivermectin in Atlantic, chinook, and coho salmon and steelhead trout," *Diseases of Aquatic Organisms*, vol. 17, pp. 107–112 (1993).
E.A. Ottesen et al., "Ivermectin in human medicine," *Journal of Antimicrobial Chemotheraphy*, vol. 34, pp 195–203 (1994).
G.L. Leibee et al., "Efficacy of Emamectin Benzoate and Bacillus Thuringiensis at Controlling Diamondback Moth (Lepidoptera:Plutellidae) Populations on Cabbage in Florida," *Florida Entomologist*, vol. 78, No. 1, pp. 82–96 (1995).
M.N. Horst et al., "Biochemical Effects of Diflubenzuron on Chitin Synthesis in the Postmolt Blue Crab Callinectes Sapidus," *Journal of Crustacean Biology*, vol. 15, No. 3, pp. 401–408 (1995).
J.I. Eral, "New drug treatment hits sealice when they are most vulnerable," *Fish Farming International*, vol. 24, No. 2 (1997).
J. Stone et al., "The efficacy of emamectin benzoate as an oral treatment of sea lice Lepeophtheirus salmonis, (Kroyer), infestations in Atlantic salmon, Salmo Salar L." *Journal of Fish Diseases*, vol. 22, No. 4, pp. 261–270 (Jul. 1999), XP000929817 OXFORD., GB abstract p. 263, col. 1, paragraph 3.
A. C. Chukwudebe et al., "Bioaccumulation Potential of 4"–epi–(Methylamino)–4"–deoxyavermectin B1a Benzoate (Emamectin benzoate) in Bluegill Sunfish" *Journal of Agricultural and Food Chemistry*, vol. 44, No. 9, pp. 2894–2899 (1996), XP000929642 American Chemical Society. Washington, US ISSN 0021–8561, p. 2894, col. 1, p. 2896, col. 1, figure 3.

*Primary Examiner*—Elli Peselev
(74) *Attorney, Agent, or Firm*—Arthur Mann; Pamela G. Salkeld; William Y. Lee

(57) ABSTRACT

A method of eliminating, reducing or preventing parasites in a fish population is provided by feeding emamectin or a salt thereof to the fish population at a daily dose of 25 µg to 400 µg per kg of fish biomass per day for a period of 3–14 days. Also provided is a kit for preparing a medicated fish feed for eliminating, reducing or preventing parasites in a fish population, the kit having a supply of emamectin or a salt thereof and printed instructions for feeding the emamectin or emamectin salt at a daily dose of 25 µg to 400 µg per kg of fish biomass per day for a period of 3–14 days.

10 Claims, 4 Drawing Sheets

METHOD OF USING EMAMECTIN TO TREAT FISH PARASITES

This application claims the benefit of U.S. Provisional Application No. 60/128,255, filed Apr. 8, 1999.

BACKGROUND OF THE INVENTION

The control of sea lice (*Lepeophtheirus salmonis* and *Caligus elongatus*) infestations in commercial salmon farming operations is still largely dependent on the use of chemical treatments (Roth M., Richards R. & Sommerville C. (1993) "Current Practices In The Chemotherapeutic Control of Sea Lice Infestations: A Review" *Journal of Fish Diseases* (16(1): 1–26). Outbreaks of these ectoparasitic copepods are currently treated by immersion bath treatments, with the organophosphates dichlorvos (Aquagard® Novartis) and Azamethiphos (Salmosan® Novartis), or hydrogen peroxide (Salartect® Brenntag, Paramove® Solvay-Interox) or the synthetic pyrethoids, cypermethrin (Excis® Vericore) and deltamethrin (Alphamax® Alpharma). Bath procedures are very labor intensive, costly and cause considerable stress to fish. Further, such treatments may not be feasible on exposed sites and during adverse weather conditions.

With the exception of cypermethrin, (Jakobsen P. J. & Holm J. C. (1990) "Promising Test With New Compound Against Salmon Lice" *Norsk Fiskeoppdrett*. January, 16–18), bath treatments are only effective against pre-adult and adult stages of sea lice, allowing chalimus stages to survive and continue the cycle of infestation. Treatments are therefore indicated only when populations reach the pre-adult and adult phases, and thus must be repeated frequently for effective control. Resistance to the organophosphate dichlorvos has been identified in some populations of sea lice (Jones M. W., Sommerville C. S. & Wootten, R. (1992) "Reduced Sensitivity of the Salmon Louse, *Lepeophtheirus salmonis*, to the Organophosphate Dichlorvos" *Journal of Fish Diseases* 15:197–202). Hydrogen peroxide may cause damage to the gills and its use is restricted in summer owing to its toxicity at higher water temperatures (Thomassen J. M. (1993) "Hydrogen peroxide as a Delousing Agent for Atlantic Salmon" In: *Pathogens of Wild and Farmed Salmon: Sea Lice* (ed. by G. Boxshall & D. Defaye) Ellis Horwood Ltd. London).

A treatment that is effective against all parasitic stages of sea lice and other parasites which could be administered in feed, to avoid the disadvantages associated with bath applications, would be beneficial to the salmon industry. In-feed treatment allows medication during adverse weather conditions and on exposed sites and will permit simultaneous medication of all cages on a site and all sites in a loch system or single bay, thus reducing any cross infestation that may occur during the several days necessary to apply bath treatments to all cages on a site. The in-feed treatments currently available are the insect growth regulators, diflubenzuron (Lepsidon® Ewos) and teflubenzuron (Calicide® Nutreco) (Erdal J. I. (1997) "New Drug Treatment Hits Sea Lice When They are Most Vulnerable". *Fish Farming International* vol.24, No.2). Their mode of action is the inhibition of chitin synthesis (Horst M. N. & Walker A. N. (1996) "Biochemical Effects of Diflubenzuron on Chitin Synthesis in the Post-molt blue crab" (*Callinectes sapidus*) *Journal of Crustacean Biology.* 15: 401–408) and activity is therefore restricted to the moulting stages of sea lice.

The avermectins, produced by the culture of *Streptomyces avermilitis*, have highly potent anthelmintic and insecticidal properties. A chemically modified derivative, ivermectin (22,23-dihydroavermectin $B_1$) was developed as a broad spectrum anti-parasitic for cattle, sheep, horses and pigs (Sutherland I. H. (1990) "Veterinary Use of Ivermectin" *Acta Leidensia* 59: 211–216) and has been marketed worldwide since 1981. Ivermectin has also been extensively used in the treatment of several human parasitoses (Ottesen E. A. & Campbell W. C. (1994) "Ivermectin in Human Medicine" *Journal of Antimicrobial Chemotherapy.* 34(2): 195–203). Following the recognition of organophosphate resistance in sea lice (Jones M. W., Sommerville C. S. & Wootten, R. (1992) "Reduced Sensitivity of the Salmon Louse, *Lepeophtheirus salmonis,* to the Organophosphate Dichlorvos" *Journal of Fish Diseases* 15:197–202), ivermectin was considered as an alternative therapy. In addition to its novel mode of action, a further advantage lay in its application as an in-feed medication. Although ivermectin has not received regulatory approval for use in salmon, it may be prescribed in the United Kingdom by veterinarians under the cascade procedure (Anonymous (1998) *Amelia* No.8 Veterinary Medicines Directorate. Woodham Lane, Newhaw, Addlestone, Surrey KT15 3NB), where authorised products fail to provide effective control of sea lice infestations. The use of ivermectin over several years has indicated that it exercises some control at the commonly adopted dose rate of 25 μg $kg^{-1}$ biomass twice weekly (Rae G. H. (1996) "Guidelines for the Use of Ivermectin Pre-Mix for Pigs to Treat Farmed Salmon For Sea Lice" Scottish Salmon Growers Association pamphlet). However, ivermectin has been found to be toxic at levels greater than 25 μg $kg^{-1}$ biomass twice weekly (S. C. Johnson, et al., "Toxicity and Pathological Effects of Orally Administered Ivermectin In Atlantic, Chinook, and Coho Salmon and Steelhead Trout," *Diseases of Aquatic Organisms.* Vol. 17: 107–112 (1993).

Emamectin (4"-deoxy-4" epimethylaminoavermectin $B_1$) has been recently used for treating edible plant crops (Leibee G. L., Jansson, R. K., Nuessly, G & Taylor J. L. (1995) "Efficacy of Emamectin Benzoate and *Bacillus thuringensis* at Controlling Diamondback Moth (Lepidoptera: Plutellidae) Populations On Cabbage in Florida" *Florida Entomologist.* 78(1): 82–96).

SUMMARY OF THE INVENTION

This invention provides a method of eliminating, reducing, or preventing parasites in a fish population, comprising feeding emamectin or a salt thereof to said fish population at a daily dose of 25 μg to 400 μg per kg of fish biomass per day for a period of 3–14 days.

In a further aspect, a kit for preparing a medicated fish feed for eliminating, reducing or preventing parasites in a fish population is provided, comprising a supply of emamectin or a salt thereof and printed instructions for feeding the emamectin or emamectin salt at a daily dose of 25 μg to 400 μg per kg of fish biomass per day for a period of 3–14 days.

DETAILED DESCRIPTION OF THE INVENTION

Figure 1:
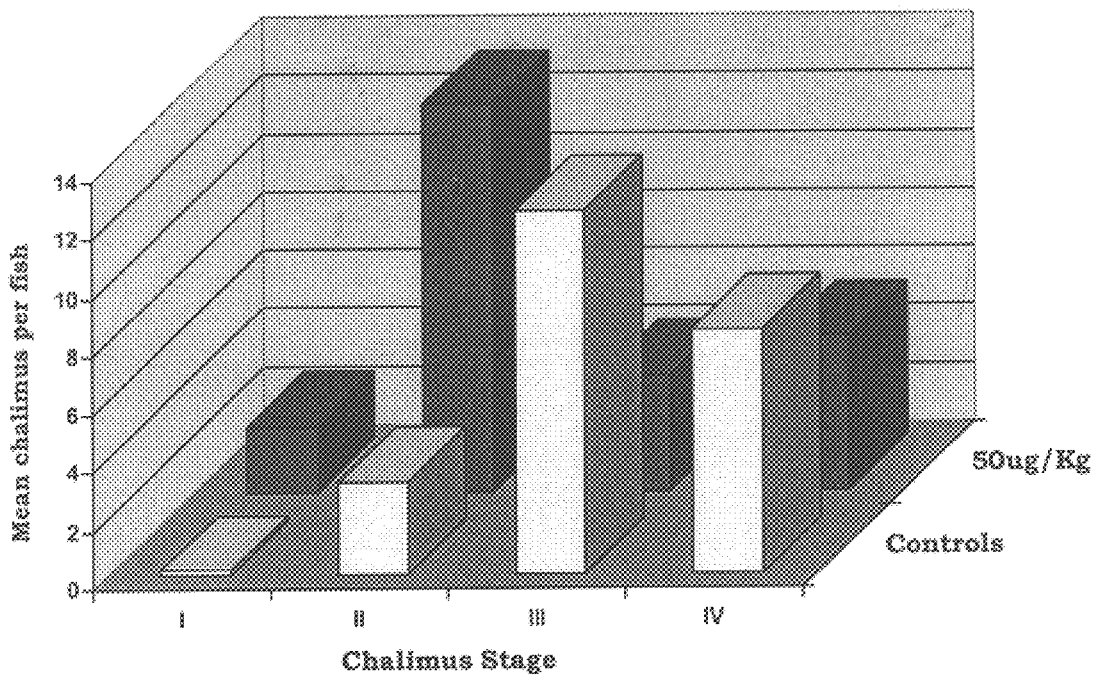
FIG. 1 is a chart comparing the mean individual chalimus (stages I, II, III and IV) per fish for the control group versus the group dosed at 50 μg/kg at day 7 for the dose titration study (Example 1).

Emamectin (4"-deoxy-4" epimethylaminoavermectin $B_1$), which can be prepared as described in U.S. Pat. No. 5,288,710 or 5,399,717, is a mixture of two homologues, 4"-deoxy-4"-epi-methylaminoavermectin B1a and 4"-deoxy-4"-epi-methylaminoavermectin B1b. Preferably, a salt of emamectin is used. Non-limiting examples of salts of emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the emamectin salt used in the present invention is emamectin benzoate.

It has been surprisingly discovered that emamectin, when used at the dosage levels and the dosage schedule in accordance with this invention, is not toxic to fish populations. This is a particularly surprising discovery, given the fact that ivermectin has been found to be toxic at relatively low levels. Because ivermectin can not be administered on consecutive days due to toxicity concerns, there is a substantial risk that not all fish in a given population will receive an appropriate dose due to over agressive feeders. The ability to feed emamectin over at least several consecutive days is a significant advantage over ivermectin, because feeding over several days increases the likelihood that more fish in a given population will consume it.

Emamectin and its salts may be used in accordance with the present invention to eliminate or reduce all types of fish parasites, including ectoparasites, as well as endoparasites. Examples of endoparasites that can be eliminated or reduced, include, but are not limited to: those belonging to the Phylum Platyhelminthes (Classes Monogenea, Digenea, and Cestoda); the Phylum Aschelminthes (Class Nematoda); and protozoans (e.g., myxozoan infections (Phylum Mxyozoa), microsporidian infections (Phylum Microspora), coccidian infections (Phylum Apicomplexa), and the Phylum Ciliophora). Examples of ectoparasites that can be eliminated or reduced, include, but are not limited to: monogeneans; parasites from the Phylum Arthropoda (Class Crustacea, Subclass Branchiura, and Subclass Copepoda (e.g., including the Orders Cyclopidea, Caligidea, and Lernaeopodidea)); and parasites from the Order Argulus and the Phylum Isopoda.

The emamectin treatment of the present invention has been found to be particularly effective as a treatment for sea lice, i.e., parasites belonging to the Subclass Copepoda, Order Caligidea, especially those belonging to the genera Lepeophtheirus and Caligus.

Any fish species, including fresh water and salt water varieties, can be treated with emamectin to eliminate or reduce parasites. Examples of fish that can be treated include, but are not limited to: salmon, trout, catfish, sea bass, tuna, halibut, arctic charr, sturgeon, turbot, flounder, sole, carp, tilapia, striped bass, eel, sea bream, yellowtail, amberjack, grouper and milkfish.

The dose of emamectin that is effective for reducing, eliminating, or preventing parasites can be routinely determined by a veterinarian, although it may vary depending on the species of fish treated, the particular parasites involved, and the degree of infestation. Preferably, emamectin or a salt thereof is fed at a dose of 25 $\mu$g to 400 $\mu$g per kg of fish biomass per day, more preferably, 25 $\mu$g to 100 $\mu$g per kg of fish biomass per day, most preferably, 50 $\mu$g to 75 $\mu$g per kg of fish biomass per day.

The emamectin treatment is administered daily, for a period of 3 to 14 days, preferably for 7–14 days, most preferably for 1 week. It has been surprisingly discovered that emamectin exhibits sustained efficacy of up to 8 to 10 weeks after treatment. Thus, emamectin can be administered as a prophylactic measure to prevent the occurrence of parasites.

The kit in accordance with the present invention may be in any form suitable for providing a supply of emamectin for at least 7 days, together with written instructions for administering it according to the dosing levels and schedule described above. Examples include, but are not limited to, various containers (e.g., bottles, cartons, blister packs, and ampules) either accompanied by a package insert describing the cyclical dosing instructions, or wherein the dosing instructions are printed on, or affixed to the container. The emamectin or emamectin salt in the kit may be in the form of a pre-mix, comprising one or more diluents and 0.01 to 1% by weight of the emamectin or emamectin salt.

The medicated fish feed may be prepared by incorporating a suitable amount of emamectin or a salt thereof into a commercially available fish feed product to achieve the desired dosing levels. The amount of emamectin incorporated into the fish feed will depend on the rate at which the fish are fed. For fish fed at the rate of 0.2% to 4% of biomass/day, the medicated feed preferably contains from 0.5 to 100 mg of emamectin or a salt thereof per kg of medicated feed, more preferably, from 1 to 50 mg per kg of medicated feed, and most preferably, from 5 to 15 mg per kg of medicated feed.

Although emamectin can be incorporated into a feed mixture prior to pelleting, the medicated feed is preferably formed by coating feed pellets with emamectin. For coating feed pellets, it is preferable to use a pre-mix containing:

(a) 0.01 to 1% by weight emamectin or a salt thereof,
(b) 0.001 to 0.2% by weight of a preservative;
(c) 1 to 4% by weight of propylene glycol or polyethylene glycol; and
(d) QS diluent.

The preservative is preferably butylated hydroxyanisole (BHA). Preferably, propylene glycol is used. The diluent may be any of the commonly used diluents, e.g., lactose, maltodextrin, cornstarch, calcium carbonate, microcrystalline cellulose, rice hulls, and corn cob. Preferably, the diluent is maltodextrin, cornstarch, or a mixture thereof. A particularly preferred premix contains 0.2 wt. % emamectin benzoate, 0.01 wt. % butylated hydroxyanisole, 2.5 wt. % propylene glycol, 49.8 wt. % cornstarch, and QS maltodextrin M-100. The pre-mix is preferably prepared using a high-shear mixer/granulator using the following procedure: Dissolve BHA in propylene glycol under stirring. Charge starch to a high-shear mixer/granulator. Charge the BHA solution slowly to the starch under mixing. Continue mixing for 20–40 minutes (target 30 min) to allow the starch to absorb the solution. Scrape the interior wall of the mixing bowl to remove any adhered materials. Charge the drug, through a 20-mesh screen, to the mixer bowl. Mix and chop (chopper turned on) for 10 minutes. Charge the Maltodextrin to the mixer bowl and mix/chop for additional 10 minutes. Discharge for packaging.

Alternatively, the following ribbon-blender process may be used: Dissolve the BHA in propylene glycol under stirring. Charge the starch to a smaller ribbon blender (approx. half batch size). Turn on the ribbon blender and slowly charge the BHA solution to the starch. Mix until uniform. Stop the mixer and let the blend stay in the mixer for about 30–60 minutes. Take out a small amount of the blend (1–5% of batch volume) into a small planetary mixer. Charge the drug to the planetary mixer and mix for 5 minutes. Transfer the drug pre-blend back to the ribbon blender and mix for 10–30 minutes. Discharge the drug blend from the ribbon blender and pass through a comminuting mill (Fitzmill) to break-up lumps. Transfer milled material to another ribbon blender. Charge the maltodextrin to the blender and mix for 10–30 minutes. Discharge for packaging.

The feed pellets can be coated with the pre-mix by either a dry-coating method or an oil coating method. In the dry-coating method, the pre-mix is mixed with the pellets so that it is uniformly distributed onto the pellets, and heated fish or vegetable oil is added to the mixture to thoroughly coat the pellets. In the oil-coating method, the pre-mix is first mixed with a small volume of heated fish or vegetable oil, which is then mixed with the pellets to uniformly disperse it onto them, and additional heated fish or vegetable oil is added to the coated pellets and mixed until the pellets are thoroughly coated.

The following examples illustrate the foregoing invention, although such examples should not be construed as limiting the scope of the invention.

EXAMPLES

Three studies were carried out at the Institute of Aquaculture Marine Environmental Research Laboratory in Machrihanish, Scotland. Atlantic salmon, *Salmo salar* L., post-smolts were obtained from a disease free stock and acclimatised at the test facility.

Fish were held in replicate groups in plastic fiber tanks, each with a volume of $0.54 \text{ m}^3$. Each tank was supplied with natural sea water at ambient temperature (7–14° C.) and salinity (30–35 ppt), at flow rates of approximately 18 l. $\text{min}^{-1}$. The tanks were fitted with mesh screens over the water outlet to retain uneaten fish pellets. Fish were observed daily for behavior and adverse drug reactions. Fish mortalities and the occurrence of gross sea lice damage were also recorded.

Sea Lice Infestations

Sea lice were collected during harvesting on commercial salmon farms on the west coast of Scotland. Egg strings collected from gravid female lice were incubated in sea water at ambient temperature and within a salinity range of 32–35 ppt. Once the hatched larvae reached the copepodite stage, 38–170 copepodites per fish were introduced into each of four replicate tanks of fish and the water supply to each tank was turned off for approximately three hours to allow attachment of copepodites to the fish. This was repeated 4–5 times at intervals of 3–5 days until chalimus stages I, II, III and IV were present. Chalimus numbers were evaluated at day –1 or day –2 pre-treatment, on sub-samples of fish (N=6–9 fish per tank). At this point, fish were infested with pre-adult and adult lice, by adding 5–10 lice per fish to each tank. Water supplies to each tank were turned off for around one hour until all the lice had attached to the fish. Pre-treatment lice numbers were based on a sub-sample of the total population and presented as the mean number of chalimus per fish. Fish were then randomly re-distributed from the four original tanks to each control or treatment tank, as described in the experimental design for each study, and no further infestations were carried out during or after treatment.

Medicated Feed

The basal ration was Fulmar™ (BOCM Pauls Ltd.) 3.5 or 5 mm salmon feed pellets. Emamectin benzoate was dissolved in propylene glycol and mixed with fish oil prior to top coating the feed pellets. Control feeds were prepared in the same way with propylene glycol and fish oil. Treatment was administered at nominal dose rates of 0, 25, 50 and 100 $\mu\text{g kg}^{-1}$ fish biomass per day, at a feed rate of 0.5% biomass, for a period of seven consecutive days (days 0–6). Actual daily feed consumption was measured in each tank by collecting the uneaten feed pellets approximately thirty minutes after administration and subtracting the number of pellets from the daily ration fed. The mean dose consumed was calculated for each group as follows:

$$\frac{\text{Sum of daily \% feed consumption}}{7 \text{ days}} = \text{Mean feed consumption (\%)}$$

Mean feed consumption (%)×nominal dose rate ($\mu\text{g·kg}^{-1}$)=Mean dose consumed ($\mu\text{g·kg}^{-1}$)

Evaluation of Sea Lice

Evaluation of sea lice numbers was carried out at 7, 14 and 21 days from the start of treatment. Fish were anaesthetised in 40 $\text{mg·l}^{-1}$ ethyl-P-aminobenzoate (benzocaine) and each fish examined under a low power microscope. Lice were identified as chalimus I–IV, pre-adult I or II and adult stages. Pre-adults and adult lice were additionally identified as males or females. The numbers of each developmental stage were recorded. Any lice which detached in the anaesthetic solution were included in the counts and reattached to the fish after transferring them to fresh seawater. The fish were returned to the holding tanks after sampling and the same fish were evaluated at days 7, 14 and 21.

Example 1

Dose Titration Study

The water temperature was 7–10° C. and salinity was 33–34 ppt. Pre-treatment, mean fish weights were 192 g (±30 g S.D). Emamectin benzoate was administered at nominal daily dose rates of 0, 25, 50 and 100 $\mu\text{g kg}^{-1}$ fish biomass. There were two replicate tanks per treatment with a sample size of 19 or 20 fish per tank. The results of this study are reported in Table 1, below.

TABLE 1

Dose titration study: Efficacy of emamectin benzoate against induced infestations of sea lice, *Lepeophtheirus salmonis*, on Atlantic salmon, *Salmo salar*,. Fish received medicated feed at the rate of 0.5% biomass per day for 7 consecutive days (Day 0–Day 6). The mean number of sea lice was determined on days 7, 14 and 21. The mean and standard deviation are derived from the pooled data of two replicate tanks (sample size N = 19 or 20 fish per tank).

| Time | Nominal dose $\mu g \cdot kg^{-1}$ | Mean dose* consumed $\mu g \cdot kg^{-1}$ | Mean Total lice (± S.D) | Mean chalimus (± S.D) | Mean motiles (± S.D) | % Reduction relative to controls (Total lice) |
|---|---|---|---|---|---|---|
| Day 7 | 0 | 0 | 51.1 ± 15.1 | 24.3 ± 8.8 | 26.7 ± 7.8 | / |
| | 25 | 21.5 | 32.6 ± 10.7 | 20.9 ± 8.6 | 11.7 ± 6.0 | 36.2% |
| | 50 | 45.0 | 31.9 ± 11.4 | 24.8 ± 10.3 | 7.1 ± 4.1 | 37.5% |
| | 100 | 91.0 | 33.0 ± 10.7 | 29.0 ± 9.8 | 4.0 ± 3.6 | 35.4% |
| Day 14 | 0 | | 44.9 ± 11.1 | 3.2 ± 2.0 | 41.7 ± 10.5 | / |
| | 25 | | 13.1 ± 6.9 | 9.7 ± 3.9 | 3.4 ± 6.4 | 70.8% |
| | 50 | | 13.4 ± 5.9 | 12.4 ± 3.5 | 1.0 ± 1.2 | 70.3% |
| | 100 | | 15.1 ± 5.8 | 14.1 ± 5.5 | 1.0 ± 3.2 | 66.4% |
| Day 21 | 0 | | 34.5 ± 9.3 | 0.03 ± 0.2 | 34.5 ± 9.3 | / |
| | 25 | | 3.5 ± 2.7 | 2.4 ± 1.9 | 1.1 ± 2.2 | 89.8% |
| | 50 | | 1.7 ± 1.3 | 1.6 ± 1.5 | 0.1 ± 0.3 | 95.2% |
| | 100 | | 1.5 ± 1.6 | 1.2 ± 1.2 | 0.3 ± 1.0 | 95.8% |

*Mean dose consumed is the actual dose received calculated from the percentage feed consumption during the medication period.

Example 2
Dose Confirmation Study I

The water temperature was 12–14° C. and salinity was 33–35 ppt. Pre-treatment, mean fish weights were 224 g (±43 g S.D). Emamectin benzoate was administered at nominal daily dose rates of 0, 25, and 50 $\mu g \cdot kg^{-1}$ biomass. There were three replicate tanks per treatment with 15 fish per tank. However, in this study, fish mortalities reduced the number of fish available for parasite evaluation by the end of the study to 9, 19 & 14 in the 25 $\mu g \cdot kg^{-1}$ groups, 10, 12 & 13 in the 50 $\mu g \cdot kg^{-1}$ groups and only 2, 5 & 5 groups. For this reason a second study, dose confirmation II (Example 3, below) was carried out. The results of this study are reported in Table 2, below.

TABLE 2

Dose Confirmation study I: Efficacy of emamectin benzoate against induced infestations of sea lice, *Lepeophtheirus salmonis*, on Atlantic salmon, *Salmo salar*,. Fish received medicated feed at the rate of 0.5% biomass per day for 7 consecutive days (Day 0–Day 6). The mean number of sea lice was determined on days 7, 14 and 21. The mean and standard deviation are derived from the pooled data of the three replicate tanks (sample size N = 2–15 fish per tank).

| Time | Nominal dose $\mu g \cdot kg^{-1}$ | Mean dose* consumed $\mu g \cdot kg^{-1}$ | Mean Total lice (± S.D) | Mean chalimus (± S.D) | Mean motiles (± S.D) | % Reduction relative to controls (Total lice) |
|---|---|---|---|---|---|---|
| Day 7 | 0 | 0 | 60.9 ± 15.1 | 1.9 ± 1.6 | 59.0 ± 14.9 | / |
| | 25 | 20.2 | 34.2 ± 15.8 | 1.8 ± 1.7 | 32.4 ± 15.4 | 43.8% |
| | 50 | 44.3 | 28.1 ± 13.1 | 3.2 ± 2.2 | 24.9 ± 13.2 | 53.8% |
| Day 14 | 0 | | 40.9 ± 14.4 | 0 | 40.9 ± 14.4 | / |
| | 25 | | 9.8 ± 4.4 | 0.30 | 9.5 ± 4.4 | 76.0% |
| | 50 | | 4.9 ± 2.7 | 0.6 | 4.3 ± 2.6 | 88.0% |
| Day 21 | 0 | | 27.3 ± 9.7 | 0 | 27.3 ± 9.7 | / |
| | 25 | | 4.9 ± 3.1 | 0 | 4.9 ± 3.1 | 81.9% |
| | 50 | | 1.6 ± 1.3 | 0 | 1.6 ± 1.4 | 94.3% |

*Mean dose consumed is the actual dose received calculated from the percentage feed consumption during the medication period.

Example 3
Dose Confirmation Study II

The water temperature was 9–12° C. and salinity was 30–34 ppt. Pre-treatment, mean fish weights were 418.2 g (±49 g S.D). Emamectin benzoate was administered at se rates of 0 and 50 $\mu$g kg$^{-1}$ biomass. There were three replicate tanks per treatment with a sample size of 15–16 fish per tank. The results of this study are reported in Table 3, below.

for each set of replicate tanks to be pooled in Tables 1, 2 and 3. However, data were also analyzed separately for each replicate tank.

TABLE 3

Dose Confirmation study II: Efficacy of emamectin benzoate against induced infestations of sea lice, *Lepeophtheirus salmonis*, on Atlantic salmon, *Salmo salar*,. Fish received medicated feed at the rate of 0.5% biomass per day for 7 consecutive days (Day 0–Day 6). The mean number of sea lice was determined on days 7, 14 and 21. The mean and standard deviation are derived from the pooled data of the three replicate tanks (sample size N = 15–16 fish per tank).

| Time | Nominal dose $\mu$g · kg$^{-1}$ | Mean dose* consumed $\mu$g · kg$^{-1}$ | Mean Total lice (± S.D) | Mean chalimus (± S.D) | Mean motiles (± S.D) | % Reduction relative to controls (Total lice) |
|---|---|---|---|---|---|---|
| Day 7 | 0 | 0 | 74.9 ± 17.1 | 22.7 ± 8.8 | 52.2 ± 13.4 | / |
|  | 50 | 45.7 | 40.5 ± 12.2 | 30.0 ± 11.8 | 10.5 ± 8.1 | 45.9% |
| Day 14 | 0 |  | 50.2 ± 10.3 | 0.6 ± 0.8 | 49.5 ± 10.3 | / |
|  | 50 |  | 14.7 ± 5.9 | 12.7 ± 5.7 | 2.0 ± 3.2 | 70.7% |
| Day 21 | 0 |  | 38.1 ± 8.6 | 0.1 ± 0.3 | 38.1 ± 8.7 | / |
|  | 50 |  | 2.1 ± 2.1 | 1.5 ± 1.7 | 0.6 ± 1.1 | 94.6% |

*Mean dose consumed is the actual dose received calculated from the percentage feed consumption during the medication period.

Data Handling

Results were summarised as chalimus (chalimus stages I–IV), motile lice pre-adult and adult stages) and total lice (chalimus and motile stages combined). Data on the number of lice per fish were subjected to F-tests for homogeneity of variances and a correlation test to examine the normality of distribution. Fish weights and pre-treatment lice counts were tested by one-way ANOVA. As the variances were not heterogenous or normally distributed post-treatment numbers of lice were analyzed using the non-parametric Dunn's test (Zar 1984).

In all three studies, there were no significant differences (P>0.05) in chalimus or motile lice numbers between any of the replicate tanks in each of the control, 25, 50 or 100 g kg$^{-1}$ groups at any time point. This allowed the mean data The percentage reduction in mean sea lice, relative to the control groups, was calculated for each dose as follows:

$$\% \text{ reduction} = 100 - \left(\frac{\text{Mean of treated replicates}}{\text{Mean of the control replicates}}\right).$$

A summary of the results for each of the three studies is set forth in Table 4, below.

TABLE 4

Summary data for the dose titration study, dose confirmation study I and dose confirmation study II at day 21: Efficacy of emamectin benzoate against induced infestations of sea lice, *Lepeophtheirus salmonis*, on Atlantic salmon, *Salmo salar*,. Fish received medicated feed at the rate of 0.5% biomass per day for 7 consecutive days (Day 0–Day 6).

| Study | Nominal dose $\mu$g · kg$^{-1}$ | Mean dose consumed $\mu$g · kg$^{-1}$ | % Reduction (Total lice) | Percentage of fish with no lice present (chalimus or motiles) | Percentage of fish with no motile lice present | Percentage fish mortality* |
|---|---|---|---|---|---|---|
| Dose titration study | 0 | 0 | / | 0% | 0% | 5% |
|  | 25 | 21.5 | 89.8% | 13.8% | 55.0% | 0% |
|  | 50 | 45.0 | 95.2% | 22.5% | 87.5% | 0% |
|  | 100 | 91.0 | 95.8% | 28.2% | 87.0% | 2.5% |
| Dose Confirmation Study I | 0 | 0 | / | 0% | 0% | 75% |
|  | 25 | 20.2 | 81.9% | 3.0% | 6.1% | 31% |
|  | 50 | 44.3 | 94.3% | 28.6% | 28.6% | 27% |
| Dose Confirmation | 0 | 0 | / | 0% | 0% | 6% |
|  | 50 | 45.7 | 94.6% | 27% | 66.3% | 0% |

% Reduction is the reduction in sea lice numbers relative to the control group, calculated from the pooled replicate means for each treatment group.
*Represents mortality attributed to sea lice damage, except in dose confirmation study II where 2% of the mortalities in control fish were not attibuted to sea lice. Mortality figures include culled fish.

Analysis and Discussion of Results

Feed consumption in the treated groups ranged from 81–92%. The actual mean doses consumed were calculated for each group and are presented in Tables 1, 2 and 3 along with the nominal dose rates. Feed consumption ranged from 77–90% in the control groups. Feeding behavior and activity were observed to decline in some of the control groups over the study period. This was associated with the higher lice levels on control fish and was most notable when sea lice activity increased as chalimus matured to the more destructive motile stages. There were no significant differences (P>0.05) in mean fish weights between any of the treatment and control groups, at the end of each study.

No adverse effects or fish mortality were attributed to treatment with emamectin benzoate at any of the doses tested. There were few fish mortalities in the dose titration study or the dose confirmation study II but, because of high lice numbers, a number of mortalities or culls occurred in dose confirmation study I (Table 4).

Dose Titration Study

At the start of the study, the overall pre-treatment mean number of chalimus per fish, based on a sub-sample of ten fish per tank, was 58.1 (±21.9). There were no significant differences ($F_{3,36}$=1.70, P>0.05) in infestation levels between tanks prior to re-distribution and treatment. The pre-treatment mean number of lice, including motiles, was 63–68 per fish.

The results of the dose titration study are shown in Table 1. As early as day 7, the total numbers of lice per fish were reduced by 35.4–37.5% in all treatment groups, compared to the control groups. By day 21, the mean number of lice per fish was reduced by 89.8, 95.2 and 95.8% respectively in the 25, 50 and 100 $\mu$g kg$^{-1}$ groups. The control groups had a mean of 34.5 lice per fish, while at a dose of 50 $\mu$g kg$^{-1}$, the mean was as low as 1.7. Numbers of lice relative to the control groups were significantly reduced at both 50 and 100 $\mu$g kg$^{-1}$ dose rates at 7, 14 (P<0.05) and 21 (P<0.001) days from the start of treatment. However, there was no significant difference between the dose rates of 50 and 100 $\mu$g kg$^{-1}$.

The data were also analysed separately for the chalimus and motile stages and showed that from day 7 to day 21 the mean number of motile lice increased in the control groups from a mean of 26.7 to 34.5 per fish, as the chalimus matured (Table 1). In contrast, the mean numbers of motile lice in the treated groups fell to as low as 0.1–1.1 per fish at day 21.

Figure 2:
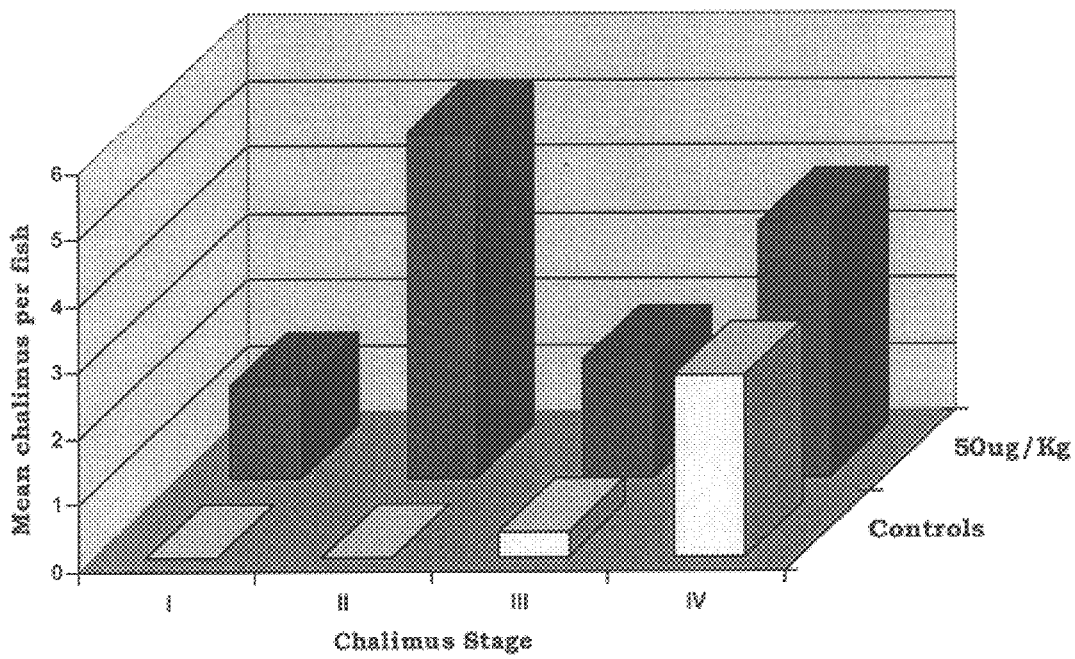
FIG. 2 is a chart showing the same comparison as FIG. 1, but at day 14.

Mean numbers of chalimus also declined in the control groups as they matured, resulting in an increase in the number of motile stages (Table 1). However, in all three treated groups, the mean number of chalimus declined more slowly and there was no corresponding increase in the number of motile stages. At days 14 and 21, chalimus numbers were higher in all three treated groups than in the control groups. However, many of the chalimus present on treated fish were abnormal in appearance and were considered to be dead or non-viable. At day 7, there were more chalimus I and II stages on treated fish than on control fish, which had a higher proportion of chalimus III and IV stages as shown in FIG. 1. At day 14 (FIG. 2), there were still chalimus I and II stages present on treated fish, while control fish had no chalimus I or II and only a few chalimus III and IV stages remaining.

At day 21, many of the treated fish had no motile lice present, while some fish were completely free of both chalimus and motile lice. In contrast, none of the control fish was completely free of motile lice (Table 4).

Dose Confirmation Study I

At the start of the study, the overall pretreatment mean number of chalimus per fish, based on a sub-sample of nine fish per tank, was 82.3 (±36.6). There were no significant differences ($F_{3,32}$=0.55, P>0.05) in infestation levels between tanks prior to re-distribution and treatment. The pretreatment mean total number of lice, including motiles, was 87–92 per fish.

In this study, a number of fish died or were culled as a result of the high infestation levels achieved. In the control groups, where lice numbers remained high, 75% of fish died or were culled, while only 27% of fish treated at 50 $\mu$g kg$^{-1}$ died or were culled (Table 4). Examination of dead fish in the control groups revealed very high numbers of motile lice and, it is likely that the control fish which survived to day 21 were those with fewer lice present. Thus, the mean number of lice per fish at day 21 may have been much higher if all the control fish had survived. All mortalities and culled fish were attributed to damage inflicted by sea lice activity. Sea lice damage on both control and treated fish appeared as areas of erosion of the epidermis in the cranial and dorsal region and was accompanied by reduced feeding activity in these individuals. By day 21, the general appearance and feeding behavior of fish in the treated groups were markedly improved. In contrast, the few surviving fish in the control groups had lice damage and continued to show a reduced feed response.

The results of dose confirmation study I are shown in Table 2. In the treated groups, the total mean numbers of lice were already reduced by 44–54% at day 7, compared to the control groups and by the end of the trial at day 21, mean numbers of lice were reduced by 82% in the 25 $\mu$g kg$^{-1}$ groups and 94% in the 50 $\mu$g kg$^{-1}$ groups. At the highest dose rate of 50 $\mu$g kg$^{-1}$, sea lice numbers were significantly reduced when compared to two of the three control groups at days 14 and 21 (P<0.05). The third control replicate had a sample size of only two fish by the end of the study and was therefore not included in the analysis. Although there were no significant differences between individual replicates of the control and 25 $\mu$g kg$^{-1}$ groups, when the data were pooled to give a larger sample size, there was a significant difference (P<0.001) between these two treatments. There were also no significant differences between the 25 $\mu$g kg$^{-1}$ replicates and two of the 50 $\mu$g kg$^{-1}$ replicates, but again, when the data for these groups were pooled the two dose rates were significantly different (P<0.001). At day 21, pooled mean numbers of lice were 27.3 per fish in the control groups, 4.9 in the 25 $\mu$g kg$^{-1}$ group and 1.6 in the 50 $\mu$g kg$^{-1}$ group respectively.

Although there were relatively few pre-adult and adult motile stages present at the start of the study, numbers increased in all groups up to day 7, as chalimus stages matured (Table 2). The increase in motile lice numbers on fish in the two treated groups was less than that seen in the control groups. Between days 7 and 21, mean numbers fell in the control groups through natural mortality and, in this study, owing to the death or culling of the most heavily infested fish. In the treated groups, the reduction in mean lice numbers was even greater over time and at day 21, total lice numbers were 82–94% lower than in the control groups.

Table 2 shows that mean chalimus numbers fell in the control and 25 $\mu$g kg$^{-1}$ groups from the start of the study until day 14. At days 7 and 14, chalimus numbers were slightly higher in the 50 $\mu$g kg$^{-1}$ group but again the chalimus present on treated fish were found to be non-viable so that at day 21, there were no chalimus remaining on any of the fish examined.

At day 21, 28.6% of the fish in the 50 $\mu$g kg$^{-1}$ groups were completely free of both chalimus and motile lice (Table 4). In contrast, only 3% of fish in the 25 $\mu$g kg$^{-1}$ and none of the control fish was completely free of lice.

Dose Confirmation Study II

There were no significant differences ($F_{3,20}$=0.428, P>0.05) in infestation levels of chalimus between tanks prior to re-distribution and treatment. The pre-treatment number of lice, including motiles, was 79–84 per fish.

The summarised results presented in Table 3, show that as early as day 7, mean total numbers of lice in the 50 $\mu$g kg$^{-1}$ groups were reduced by 46% relative to the control groups and at day 21 by 95%. At day 21, control groups had an overall mean of 38.1 lice per fish while the 50 µg kg$^{-1}$ groups had a mean of only 2.1 lice per fish. Numbers of lice were significantly lower (P<0.001) in all three groups treated at 50 µg kg$^{-1}$, compared to the three control groups, at days 7, 14 and 21.

Figure 3:
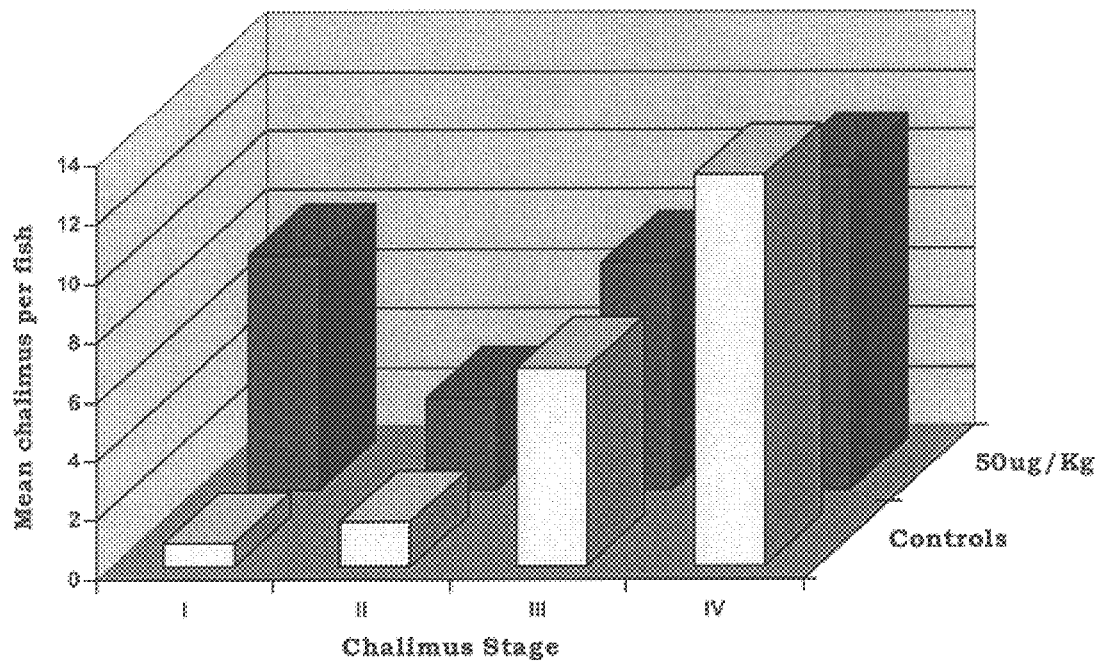
FIG. 3 is a chart comparing the mean individual chalimus (stages I, II, III and IV) per fish for the control group versus the group dosed at 50 μg/kg at day 7 for the dose confirmation study (Example 3).
Figure 4:
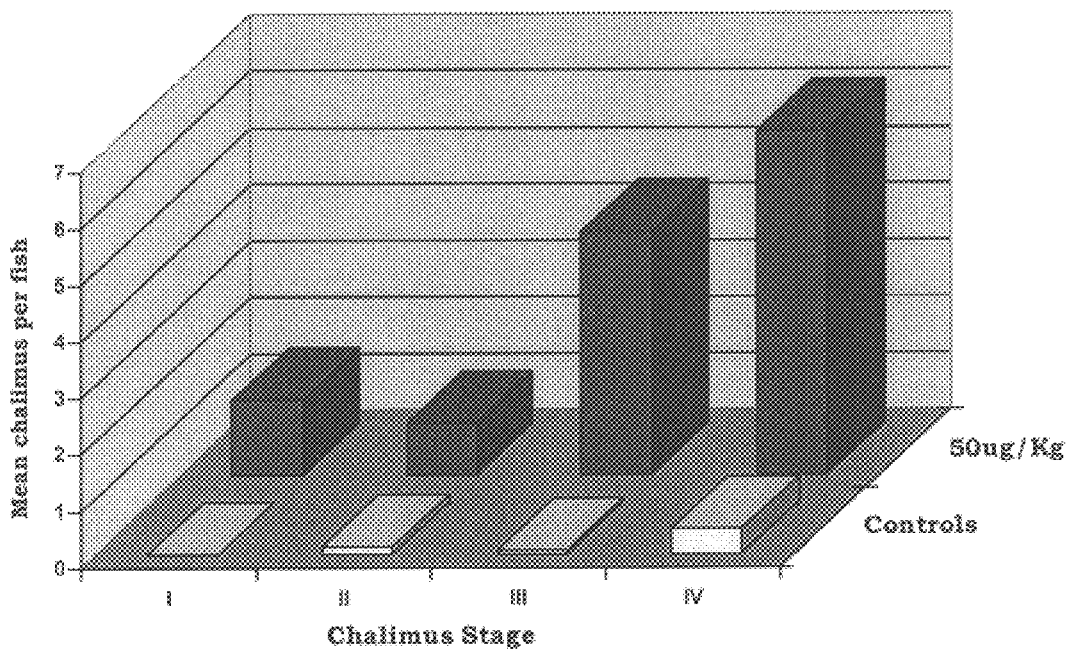
FIG. 4 is a chart showing the same comparison as FIG. 3, but at day 14.

The mean number of motile lice in the control groups showed a decline from 52.2 per fish at day 7 to 38.1 per fish by day 21 (Table 3). Over the same period the mean number of motile lice in the 50 µg kg$^{-1}$ groups fell much more rapidly and, at day 21, there was a mean of only 0.6 lice per fish. Mean chalimus numbers decreased in the control groups with maturation, so virtually no chalimus were present by day 14 (Table 3). At each sampling, more chalimus remained on treated fish than on control fish and, at day 14, this difference was statistically significant (P<0.001). At day 21, many of these chalimus persisting on treated fish were observed to be degenerate forms and were considered to be arrested in development and non-viable. FIGS. 3 and 4 show the proportions of each chalimus stage in the control and treated groups at days 7 and 14. At day 7, there was a higher proportion of chalimus I and II on treated fish while control fish had more chalimus III and IV (FIG. 3). At day 14, treated fish still had mostly chalimus stages III and IV and some stages I and II, while control fish had a mean of only 0.4 chalimus IV per fish (FIG. 4).

At the end of the study, 27% of treated fish had no chalimus or motile lice present and 66% of fish had no motile lice present. In contrast, none of the control fish were completely free of chalimus or motile lice at any stage (Table 4). By day 21, 21% of control fish had cranial lesions resulting from sea lice activity. No cranial lesions were recorded on fish in the 50 µg kg$^{-1}$ groups and there were no fish mortalities in any of the treated groups, whereas 4% of control fish were culled in this study because of sea lice damage.

Oral treatment of Atlantic salmon with emamectin benzoate showed very good efficacy against the motile and chalimus stages of L. salmonis in all three studies. Reductions in parasite numbers increased over the 21 day study period. A dose rate of 50 µg kg$^{-1}$ emamectin benzoate was found to be as effective as 100 µg kg$^{-1}$ in reducing sea lice numbers. Despite the fact that the 25 µg kg$^{-1}$ dose rate proved effective in most instances, higher reductions, of 94–95%, were consistently achieved at a dose rate of 50 µg kg$^{-1}$. In dose confirmation study I, the mean total number of lice on fish treated at 25 µg kg$^{-1}$ was not significantly different from that of the control groups, while fish treated at 50 µg kg$^{-1}$ had significantly fewer lice than fish treated at 25 µg kg$^{-1}$. In that study, groups treated with 25 µg kg$^{-1}$ received an actual dose rate of only 18.7–22.0 µg kg$^{-1}$, based on feed consumption rates. Individuals with heavy infestations at the start of the study were likely to have had a lower feed intake and thus, drug consumption and were not able to benefit fully from medication. This resulted in a relatively high mortality and culling rate in this group and, in all cases, these were attributed to lice damage. Although chalimus numbers remained higher on treated fish than on control fish, the absence of any corresponding increase in motile lice numbers and the delayed development of the different chalimus stages clearly indicates that treatment with emamectin benzoate is highly effective against the immature chalimus stages.

Following treatment at a dose rate of 50 µg kg$^{-1}$ emamectin benzoate, the percentage of fish with no motile lice present was as high as 87%. Although the percentage of fish with no lice present of any stage, was only 20–30%, most fish with lice had only chalimus stages. Even though many of the chalimus on treated fish were abnormal in appearance and considered to be dead or non-viable, they persisted on the fish as it may take some time for the attachment structure, the frontal filament, to break down and for detachment to occur. While efficacy against chalimus stages is beneficial in preventing their development to the more destructive motile stages, a rapid reduction in motile lice numbers is also important as they are much more acutely damaging to the host fish. As early as day 7, from the start of medication, motile lice numbers were reduced on fish treated with 50 µg kg$^{-1}$ by as much as 58–80%.

The removal of lice following treatment with emamectin benzoate, was shown to result in a reduction in epidermal lesions inflicted by the parasite. In dose confirmation study I, lice damage resulted in a number of mortalities and culling of fish, which reduced the validity of the study. For this reason, the study was repeated, but the results demonstrate the protective benefits of treatment with emamectin.

Most of the licensed treatments available for the control of sea lice infestations are not effective against both immature chalimus and mature motile stages (Roth, Richards & Sommerville 1993) and treatments must be carefully timed to ensure that the majority of lice are treated at a susceptible stage in the lifecycle. Larval lice may subsequently reach the reproductive adult stages so that populations are constantly regenerated. The advantage of a treatment that is effective against all parasitic stages is that lice can be controlled at any point in the life cycle thereby preventing reproduction. In-feed treatments allow simultaneous control in all cages so that treatments of entire sites and areas are possible, thus reducing the frequency of treatments.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method of eliminating or reducing parasites in a fish population, comprising feeding emamectin or a salt thereof to said fish population at a daily dose of 25 µg to 400 µg per kg of fish biomass per day for a period of 3–14 days.

2. The method of claim 1, wherein the parasites are endoparasites.

3. The method of claim 2, wherein emamectin benzoate is used.

4. The method of claim 1, wherein the parasites are ectoparasites.

5. The method of claim 4, wherein emamectin benzoate is used.

6. The method of claim 5, wherein emamectin benzoate is fed at a rate of 25 to 100 µg/kg of fish biomass/day for at least 7 days.

7. The method of claim 5, wherein emamectin benzoate is fed at a rate of 50 to 75 µg/kg of fish biomass/day for at least 7 days.

8. The method of claim 5, wherein the parasites are sea lice and the daily dose is administered for at least 7 days.

9. The method of claim 8, wherein emamectin benzoate is fed at a rate of 25 to 100 µg/kg of fish biomass/day.

10. The method of claim 9, wherein emamectin benzoate is fed at a rate of 50 to 75 µg/kg of fish biomass/day.

* * * * *